United States Patent
Cheng et al.

(10) Patent No.: US 10,458,979 B2
(45) Date of Patent: Oct. 29, 2019

(54) SOLID SUPPORTED ARTIFICIAL CELL MEMBRANE SYSTEM

(75) Inventors: Jinting Cheng, Singapore (SG); Madhavan Nallani, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 766 days.

(21) Appl. No.: 14/424,736

(22) PCT Filed: Aug. 29, 2012

(86) PCT No.: PCT/SG2012/000304
§ 371 (c)(1),
(2), (4) Date: Jun. 3, 2015

(87) PCT Pub. No.: WO2014/035333
PCT Pub. Date: Mar. 6, 2014

(65) Prior Publication Data
US 2016/0109434 A1    Apr. 21, 2016

(51) Int. Cl.
| | | |
|---|---|---|
| A61K 8/81 | (2006.01) | |
| A61K 8/18 | (2006.01) | |
| A61K 8/30 | (2006.01) | |
| B01D 69/02 | (2006.01) | |
| G01N 33/52 | (2006.01) | |
| C07K 17/08 | (2006.01) | |
| G01N 33/545 | (2006.01) | |
| G01N 33/566 | (2006.01) | |
| C08G 77/452 | (2006.01) | |

(52) U.S. Cl.
CPC ........... *G01N 33/525* (2013.01); *C07K 17/08* (2013.01); *G01N 33/545* (2013.01); *G01N 33/566* (2013.01); *C08G 77/452* (2013.01)

(58) Field of Classification Search
None
See application file for complete search history.

(56) References Cited

U.S. PATENT DOCUMENTS

| | | | | |
|---|---|---|---|---|
| 2011/0259815 A1* | 10/2011 | Montemagno | ......... | B01D 69/02 210/500.23 |
| 2012/0129270 A1* | 5/2012 | Nallani | ................ | C08G 65/329 436/501 |

FOREIGN PATENT DOCUMENTS

| | | | |
|---|---|---|---|
| WO | WO 01/60520 | * | 2/2001 |
| WO | 2005016259 A2 | | 2/2005 |
| WO | WO 2007/048459 | * | 5/2007 |
| WO | 2010040353 A2 | | 4/2010 |
| WO | 2010123462 A1 | | 10/2010 |

OTHER PUBLICATIONS

TNT® Quick Coupled Transcription/Translation System Technical Manual Instructions for Use of Product(s) pp. 1-32; Oct. 3, 2017.*
Chakraborty et al.,,Cellulose Microfibers as Reinforcing Agents for Structural Materials, 2006 Cellulose Nanocomposites Chapter 12, pp. 169-186.*
Hamley Nanoshells and nanotubes from block copolymers Soft Matter, 2005, 1, 36-43.*
Ho et al Simulations of Fluid Self-Avoiding Membranes Europhys. Lett., 12 (4), pp. 295-300 (1990).*
Percot et al Immobilization of Lipid Vesicles on Polymer Support via an Amphiphilic Peptidic Anchor: Application to a Membrane Enzyme Bioconjugate Chem. 2000, 11, 674-678.*
Christensen et al SensingApplications of SurfaceBased Single Vesicle Arrays Sensors 2010, 10(12), 1135211368.*
Shape—Wikipedia; pp. 1-6; downloaded on Feb 15, 2019.*
Torchilin et al., Review Structure and design of polymeric surfactant-based drug delivery systemsJournal of Controlled Release 73 (2001) 137-172.*
Ahmed et al., Polymersomes as Viral Capsid Mimics Drug Development Research 67:4-14 (2006) Research Overview.*
Juan Carlos Ybarra, "A Comparison of AB Diblock and ABA Triblock Copolymers of Polystyrene and Polyferocenylsilane for Nanolithography Applications," Submitted to the Department of Material Science and Engineering at Massachusetts Institute of Technology, Jun. 1, 2012, pp. 1-37.
Communication from European Patent Office for European Patent Application No. 12 883 541.0 dated Feb. 21, 2017, pp. 1-7.
Mitaksov et al., "Structural Engineering of pMHC Reagents for T Cell Vaccines and Diagnostics," Chemistry & Biology, vol. 14, No. 8, Aug. 2007, pp. 909-922.
Nardin et al., "Polymerized ABA Triblock Copolymer Vesicles," Langmuir, vol. 16, No. 3, 2000, pp. 1035-1041.
Percot et al, "Immunobilization of Lipid Vesicles on Polymer Support via an Amphiphilic Peptidic Anchor: Application to a Membrane Enzyme," Bioconjugate Chemistry, vol. 11, No. 5, 2000, pp. 674-678.
Yokogawa et al., "Bead-linked Proteoliposomes: A Reconstruction Method for NMR Analyses of Membrane Protein-Ligand Interactions," J American Chemical Society, vol. 127, No. 34, 2005, pp. 12021-12027.
Serena Belegrinou, PhD Thesis, University of Basel, "Solid-Supported Polymer Bilayers as Membrane Mimics," 2010, pp. 1-92.
Lin et al., "Adhesion of Antibody-Functionalized Polymersomes," Langmuir, vol. 22, No. 9, 2006, pp. 3975-3979.
Lin et al., "The Effect of Polymer Chain Length and Surface Density on the Adhesiveness of Functionalized Polymersomes," Langmuir, vol. 20, No. 13, 2004, pp. 5493-5500.

(Continued)

*Primary Examiner* — Maria G Leavitt
(74) *Attorney, Agent, or Firm* — Winstead, P.C.

(57) ABSTRACT

The present invention relates to an artificial cell membrane system comprising at least one membrane protein carrier associated with at least one membrane protein, wherein the at least one membrane protein carrier comprises or consists of a polymeric vesicle or a polymeric planar structure, and a solid support freely suspended in a fluid medium, wherein the at least one membrane protein carrier is attached to a surface of the solid support. A method of forming the artificial cell membrane system, and use of the artificial cell membrane system as a reagent are also provided.

9 Claims, 7 Drawing Sheets

(56) References Cited

OTHER PUBLICATIONS

Extended European Search Report for International Application No. PCT/SG2012/000304 dated Feb. 24, 2016, pp. 1-12.
Feng et al., "Gentle Immobilization of Nonionic Polymersomes on Solid Substrates," Langmuir, vol. 24, 2008, pp. 76-82.
Niallani et al., "Proteopolymersomes: in vitro Production of a Membrane Protein in Polymersome Membranes," Biointerphases, vol. 6, No. 4, Dec. 1, 2011, pp. 153-157.
Christensen et al., "Sensing-Applications of Surface-Based Single Vesicle Arrays," Sensors, vol. 10, No. 12, Dec. 13, 2010, pp. 11352-11368.
Grzelakowski et al., "Immobilized Protein-Polymer Nanoreactors," Small, vol. 5, No. 22, Nov. 16, 2009, pp. 2545-2548.
International Preliminary Report on Patentability for International Application No. PCT/SG2012/000304 dated Jul. 23, 2014, pp. 1-20.

\* cited by examiner (A)

(B)

US 10,458,979 B2

SOLID SUPPORTED ARTIFICIAL CELL MEMBRANE SYSTEM

TECHNICAL FIELD

The invention relates to an artificial cell membrane system, a method of forming the artificial cell membrane system, and use of the artificial cell membrane system.

BACKGROUND

In living cells, protein-protein interactions are essential in many biological processes, such as cell-cell interaction, and cell signaling. In particular, membrane proteins embedded in cell membranes, which represent 20-30% of the total proteins encoded by the human genome, play a crucial role in intra- and inter-cellular interactions, such as in diseases like cancer, diabetes mellitus, and schizophrenia, for example. In order to treat these diseases, it is critical to understand the mechanisms driving the membrane proteins involved. Although a plethora of model systems presenting the membrane proteins are available, their instability reduces their accessibility and usefulness.

Thus, membrane proteins have been widely explored and investigated as one of the most popular and viable drug targets in the pharmaceutical industry. However, working with membrane proteins is not easy, given that their amphiphilic nature requires protection from the native environment or its mimics.

Therefore, there remains a need to provide for an artificial cell membrane system which overcomes, or at least alleviates, the above problems.

SUMMARY

According to a first aspect, there is provided an artificial cell membrane system comprising at least one membrane protein carrier associated with at least one membrane protein, wherein the at least one membrane protein carrier comprises or consists of a polymeric vesicle or a polymeric planar structure, and a solid support freely suspended in a fluid medium, wherein the at least one membrane protein carrier is attached to a surface of the solid support.

According to a second aspect, there is provided a method for forming an artificial cell membrane system of the first aspect. The method comprises providing at least one membrane protein carrier, wherein the at least one membrane protein carrier comprises or consists of a polymeric vesicle or a polymeric planar structure, adding the at least one membrane protein carrier to a fluid medium containing a freely suspended solid support, and incubating the fluid medium containing a suspension of the freely suspended solid support and the at least one membrane protein carrier, thereby attaching the at least one membrane protein carrier to a surface of the freely suspended solid support, wherein at least one membrane protein is associated with the at least one membrane protein carrier either prior to the adding of the at least one membrane protein carrier to the fluid medium or after attaching the at least one membrane protein carrier to the surface of the freely suspended solid support.

According to a further aspect, there is provided use of an artificial cell membrane system of the first aspect as a reagent in a fluorescence, chemi-luminescence, or radioactivity detection technique in small molecule, antibody binding and screening assays.

BRIEF DESCRIPTION OF THE DRAWINGS

In the drawings, like reference characters generally refer to the same parts throughout the different views. The drawings are not necessarily drawn to scale, emphasis instead generally being placed upon illustrating the principles of various embodiments. In the following description, various embodiments of the invention are described with reference to the following drawings.

DESCRIPTION

The following detailed description refers to the accompanying drawings that show, by way of illustration, specific details and embodiments in which the invention may be practiced. These embodiments are described in sufficient detail to enable those skilled in the art to practise the invention. Other embodiments may be utilized and changes may be made without departing from the scope of the invention. The various embodiments are not necessarily mutually exclusive, as some embodiments can be combined with one or more other embodiments to form new embodiments.

According to a first aspect, there is provided an artificial cell membrane system comprising at least one membrane protein carrier associated with at least one membrane protein, wherein the at least one membrane protein carrier comprises or consists of a polymeric vesicle or a polymeric planar structure, and a solid support freely suspended in a fluid medium, wherein the at least one membrane protein carrier is attached to a surface of the solid support.

Figure 1:
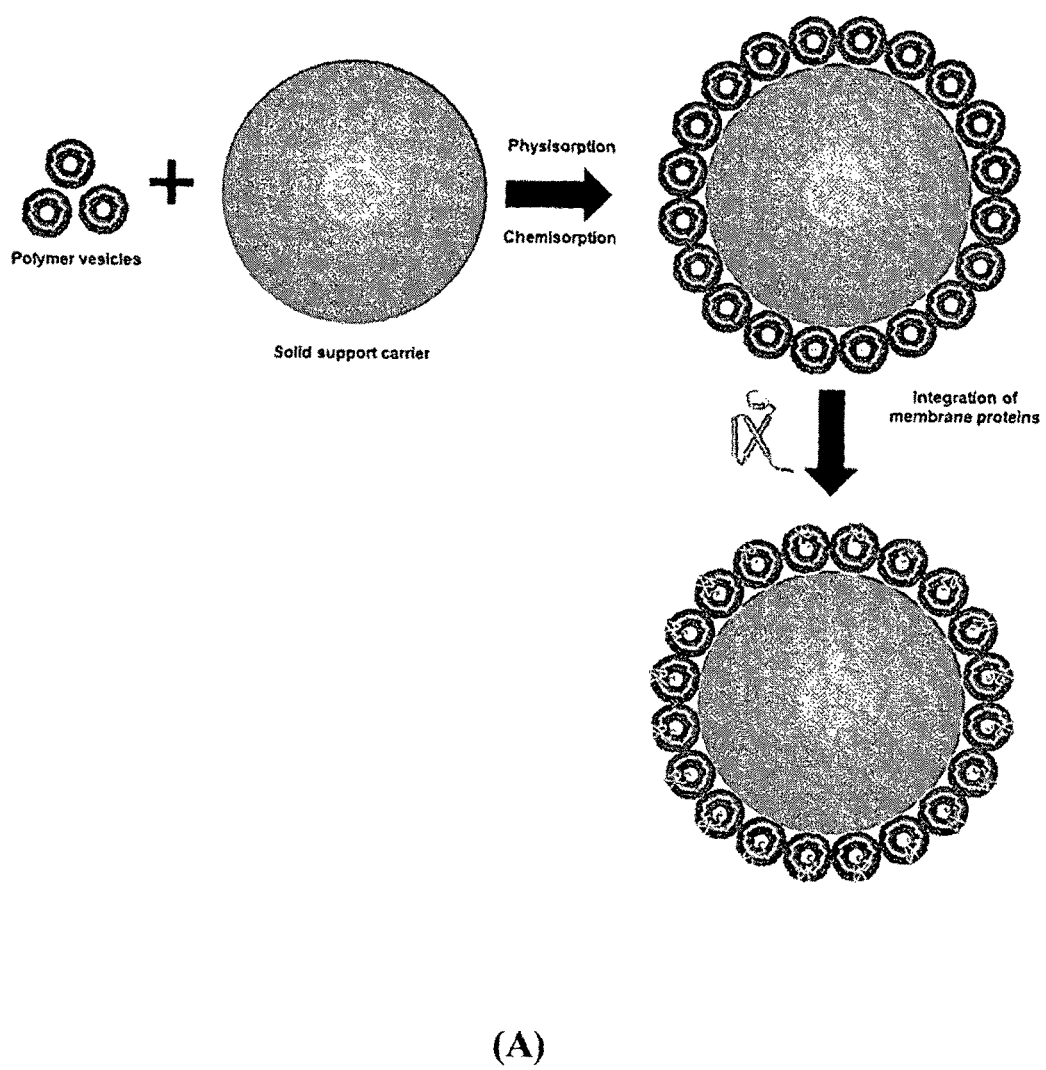
FIG. 1 shows schemes of the construction of the artificial cell membranes on free-floating 3D solid support carriers. Polymeric vesicles are attached onto the 3D surface of a free-floating solid support carrier, such as a microbead, via physisorption or chemisorption. Membrane proteins are integrated into the membranes of the supported polymeric vesicles by a method of reconstitution, insertion or spontaneous insertion via an in vitro synthesis. Polymeric vesicles (i.e. the membrane protein carriers) are attached onto the solid support (A) before or (B) after the integration of membrane proteins, resulting in proteopolymersomes or artificial cell membranes on solid support carriers.
Figure 1:
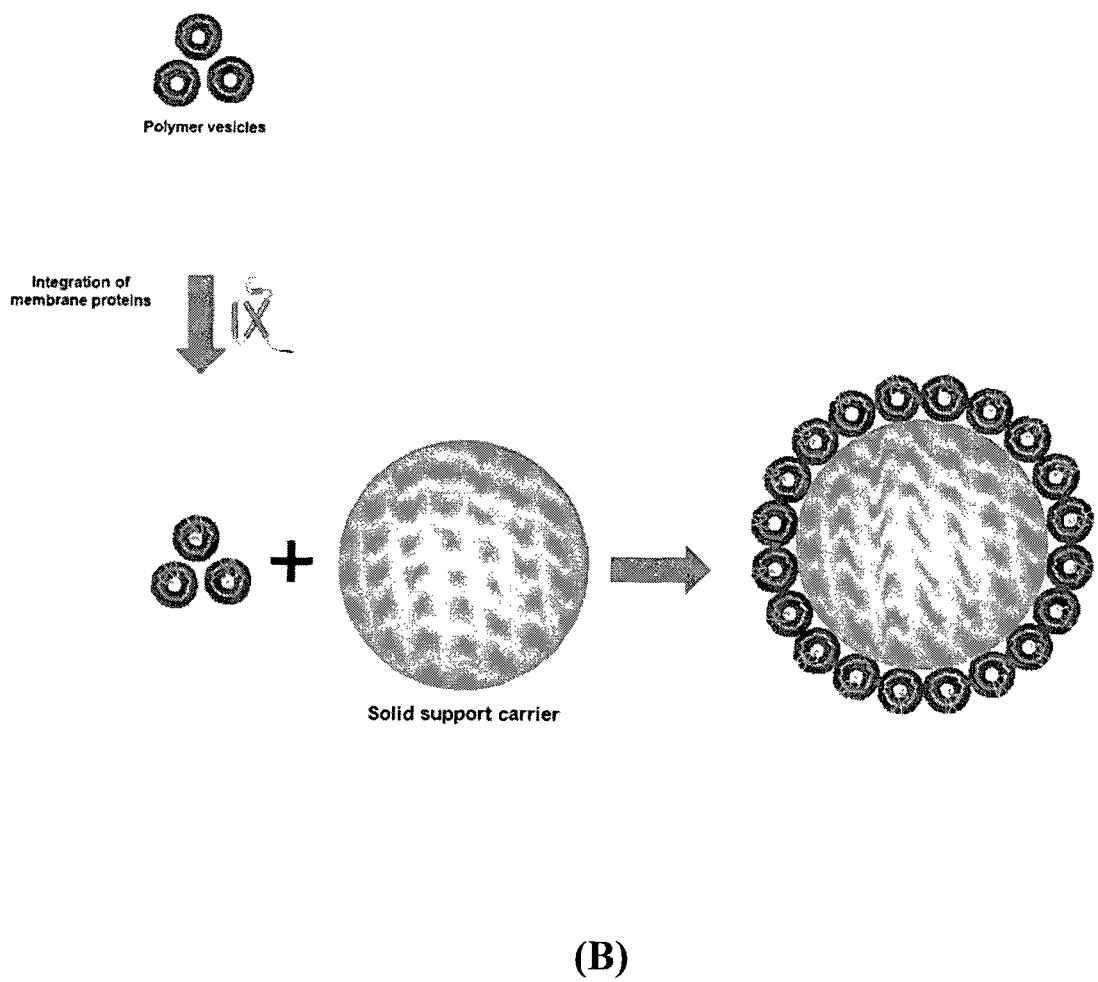

According to a second aspect as illustrated in FIGS. 1(A) and 1(B), there is also provided a method for forming an artificial cell membrane system of the first aspect. The method comprises providing at least one membrane protein carrier, wherein the at least one membrane protein carrier comprises or consists of a polymeric vesicle or a polymeric planar structure, adding the at least one membrane protein carrier to a fluid medium containing a freely suspended solid support, and incubating the fluid medium containing a suspension of the freely suspended solid support and the at least one membrane protein carrier, thereby attaching the at least one membrane protein carrier to a surface of the freely suspended solid support, wherein at least one membrane protein is associated with the at least one membrane protein carrier either prior to the adding of the at least one membrane protein carrier to the fluid medium or after attaching the at least one membrane protein carrier to the surface of the freely suspended solid support.

In the present context, a membrane protein is a protein molecule that can attach to, or otherwise associate with a membrane of a cell or an organelle. For example, this may mean that the protein or, in case it is a mutant or derivative of a natural occurring protein, its wildtype form, are in their natural environment attached or otherwise associated with a cellular membrane, including membranes of organelles and intracellular vesicles. Membrane proteins are large, amphiphilic moieties with subtle function-structure dependencies. Membrane proteins can be associated with the membrane to different degrees. A classical differentiation classified membrane proteins according to the conditions required to solubilise the same. "Peripheral" membrane proteins can be dissociated from the membrane by relatively mild conditions such as increased ionic strength or a change in pH. "Integral" membrane proteins can only be dissociated from the membrane by means of detergents or organic solvents. Such integral membrane proteins include proteins that are now known to span the entire membrane, proteins known to be partially embedded within an outer portion of the membrane such as prostaglandin $H_2$ Synthase-1, but also some proteins that interact with the membrane via hydrophobic post-translational modifications such as heterotrimeric G proteins.

Any suitable membrane protein may be used in the present artificial cell membrane system, and it may be a peripheral membrane protein or an integral membrane protein. In various embodiments, it may have one or more domains that span the membrane. Examples of a suitable membrane protein with a transmembrane domain include, but are not limited to, a G-protein coupled receptor, such as an odorant receptors, a rhodopsin receptor, a rhodopsin pheromone receptor, a peptide hormone receptors, a taste receptor, a GABA receptor, an opiate receptor, a serotonin receptor, a $Ca^{2+}$ receptor, melanopsin, a neurotransmitter receptor, such as a ligand gated, a voltage gated or a mechanically gated receptor, including the acetylcholine, the nicotinic, the adrenergic, the norepinephrine, the catecholamines, the L-DOPA-, a dopamine and serotonin (biogenic amine, endorphin/enkephalin) neuropeptide receptor, a ionotropic receptor such as a glutamate receptor, a receptor kinase such as serin/threonin kinase, a tyrosine kinase, a porin/channel such as a chloride channel, a potassium channel, a sodium channel, an OMP protein, an ABC transporter (ATP-Binding Cassette-Transporter) such as amino acid transporter, the Na-glucose transporter, the $Na^+$/iodide transporter, an ion transporters such as cytochrome c oxidase, ATPase Na/K, H/K, Ca, a cell adhesion receptor such as metallo protease, an integrin or a catherin.

In the present context, the at least one membrane protein carrier is a carrier of a membrane protein or a plurality of membrane proteins and the at least one membrane protein carrier comprises or consist of a polymeric vesicle: In various embodiments where the membrane is artificial, the membrane protein carrier is thus artificial and may also be termed as an artificial cell membrane. By "at least one" is meant 1, 2, 3, 4, 5, 6, 7, 8, 9, 10, 20, 30, 40, 50, 60, 70, 80, 90, 100, or more. By "a plurality of" is meant 2, 3, 4, 5, 6, 7, 8, 9, 10, 20, 30, 40, 50, 60, 70, 80, 90, 100, or more.

In embodiments where the membrane protein carriers are artificial cell membranes, the membrane protein carrier may comprise or consist of a polymeric vesicle. The polymeric vesicle may have a circumferential membrane comprised of the same or different amphiphilic block copolymer. In the present context, a polymeric vesicle is a vesicle with a polymeric membrane, which is typically, but may not necessarily be, formed from the self-assembly of dilute solutions of amphiphilic block copolymers, which can be of different types such as diblock and triblock. Polymeric vesicles may also be formed of tetrablock or pentablock copolymers. For triblock copolymers, the central block is often shielded from the environment by its flanking blocks, while diblock copolymers self-assemble into bilayers, placing two hydrophobic blocks tail-to-tail, much to the same effect. In most cases, the vesicular membrane has an insoluble middle layer and soluble outer layers. The driving force for polymeric vesicle formation by self-assembly is considered to be the microphase separation of the insoluble blocks, which tend to associate in order to shield themselves from contact with water. Polymeric vesicles possess remarkable properties due to the large molecular weight of the constitutent copolymers. Vesicle formation is favored upon an increase in total molecular weight of the block copolymers. As a consequence, diffusion of the (polymeric) amphiphiles in these vesicles is very low compared to vesicles formed by lipids and surfactants. Owing to this less mobility of polymer chains aggregated in vesicle structure, it is possible to obtain stable polymeric vesicle morphologies. In the context of the present invention, a vesicle does not refer to a vesicular structure comprising fats, oils, waxes, cholesterol, sterols, fat-soluble vitamins (such as vitamins A, D, E and K), monoglycerides, diglycerides, and phospholipids. Unless expressly stated otherwise, the term "polymersome" and "polymeric vesicle", as used hereinafter, are taken to be analogous and may be used interchangeably.

In embodiments where the membrane protein carrier comprises or consists of a polymeric vesicle, the polymeric vesicle has a circumferential membrane and an interior, which is typically defined by a single compartment. A respective vesicle can be taken to have a core-shell build-up. Generally the vesicle is spherical and the interior that is typically defined by a hydrophilic liquid. Hydrophilic ("water-loving") liquids, also termed lipophobic ("fat-hating"), contain molecules which can form dipole-dipole interactions with water molecules and thus dissolve therein. Such liquids are thus generally polar. Hydrophobic ("water-hating") liquids, also termed lipophilic ("fat-loving"), have a tendency to separate from water. Such liquids are thus generally non-polar. Examples of a hydrophilic liquid include, but are not limited to water, acetone, methanol, ethanol, propanol, isopropanol, butanol, tetrahydrofuran, pyridine, chloroform, ethylene glycol monobutyl ether, pyridine, ethyl acetate, acetonitrile, dimethylformamide, N,N-dimethyl acetamide, N-methylpyrrolidone, formic acid, formamide, and a polar ionic liquid. Examples of a polar ionic liquid include, but are not limited to, 1-ethyl-3-methylimidazolium tetrafluoroborate, N-butyl-4-methylpyridinium tetrafluoroborate, 1,3-dialkylimidazolium-tetrafluoroborate, 1,3-dialkylimidazolium-hexafluoroborate, 1-ethyl-3-methylimidazolium bis(pentafluoro-ethyl)phosphinate, 1-butyl-3-methylimidazolium tetrakis(3,5-bis(trifluoromethyl-phenyl)borate, tetrabutyl-ammonium bis(trifluoromethyl)imide, ethyl-3-methyl-imidazolium trifluoromethanesulfonate, 1-butyl-3-methylimidazolium methyl sulfate, 1-n-butyl-3-methylimidazolium ([bmim]) octylsulfate, and 1-n-butyl-3-methylimidazolium tetrafluoroborate. Examples of a non-polar liquid include, but are not limited to mineral oil, hexane, heptane, cyclohexane, benzene, toluene, dichloromethane, chloroform, carbon tetrachloride, carbon disulfide, dioxane, diethyl ether, diisopropylether, methyl propyl ketone, methyl isoamyl ketone, methyl isobutyl ketone, cyclohexanone, isobutyl isobutyrate, ethylene glycol diacetate, and a non-polar ionic liquid. Examples of a non-polar ionic liquid include, but are not limited to, 1-ethyl-3-methylimidazolium bis[(trifluoromethyl)sulfonyl]amide bis(triflyl)amide, 1-ethyl-3-methylimidazolium bis[(trifluoromethyl)sulfonyl]amide trifluoroacetate, 1-butyl-3-methylimidazolium hexafluorophosphate, 1-hexyl-3-methylimidazolium bis(tri-fluoromethylsulfonyl)imide, 1-butyl-3-methylimidazolium bis(trifluoromethylsulfonyl)-imide, trihexyl(tetradecyl)phosphonium bis[oxalato(2-)]borate, 1-hexyl-3-methyl imidazolium tris(pentafluoroethyl) trifluorophosphate, 1-butyl-3-methyl-imidazolium hexafluorophosphate, tris(pentafluoroethyl)trifluorophosphate, trihexyl(tetradecyl)-phosphomium, N"'-ethyl-N,N,N', N'-tetramethylguanidinium, 1-butyl-1-methyl pyrrolidinium tris(pentafluoroethyl)trifluorophosphate, 1-butyl-1-methyl pyrrolidinium bis(trifluoromethylsulfonyl)imide, 1-butyl-3-methyl imidazolium hexafluorophosphate, 1-ethyl-3-methylimidazolium bis(trifluoromethylsulfonyl)imide and 1-n-butyl-3-methylimidazolium.

The polymeric vesicle accordingly has an interior that is typically defined by a polar liquid. A suitable liquid may be a polar liquid, such as a polar protic liquid. A protic liquid, for example solvent, is a liquid that has, for example, a hydrogen atom bound to an oxygen as in a hydroxyl group or a nitrogen as in an amine group. More generally, any molecular liquid which contains dissociable $H^+$, such as hydrogen fluoride, is called a protic liquid. The molecules of such liquid can donate an $H^+$ (proton). Examples for polar protic liquid may be, but are not limited to, water, methanol, ethanol or acetic acid. In one embodiment of the present invention water may be used.

The interior of the polymeric vesicle may in some embodiments include an aqueous solution. Further matter may be included in a respective aqueous solution, for example dissolved or suspended therein. As an illustrative example an aqueous solution may include one or more buffer compounds. Numerous buffer compounds are used in the art and may be used to carry out the various processes described herein. Examples of buffers include, but are not limited to, solutions of salts of phosphate, carbonate, succinate, carbonate, citrate, acetate, formate, barbiturate, oxalate, lactate, phthalate, maleate, cacodylate, borate, N-(2-acetamido)-2-amino-ethanesulfonate (also called (ACES), N-(2-hydroxyethyl)-piperazine-N'-2-ethanesulfonicacid (also called HEPES), 4-(2-hydroxyethyl)-1-piperazine-propanesulfonicacid (also called HEPPS), piperazine-1,4-bis(2-ethanesulfonicacid) (also called PIPES), (2-[Tris(hydroxymethyl)-methyl-amino]-1-ethansulfonicacid (also called TES), 2-cyclohexylamino-ethanesulfonic acid (also called CHES) and N-(2-acetamido)-iminodiacetate (also called ADA). Any counterion may be used in these salts; ammonium, sodium, and potassium may serve as illustrative examples. Further examples of buffers include, but are not limited to, trietha-nolamine, diethanolamine, ethylamine, triethylamine, glycine, glycylglycine, histidine, tris(hydroxymethyl) aminomethane (also called TRIS), bis-(2-hydroxyethyl)-imino-tris-(hydroxymethyl)methane (also called BIS-TRIS), and N-[Tris(hydroxymethyl)-methyl]-glycine (also called TRICINE), to name a few. The buffers may be or be included in aqueous solutions of such buffer compounds or solutions in a suitable polar organic solvent. Further examples of matter that may be present, include salts, detergents or chelating compounds. As a further illustrative example an aqueous solution may include one or more compounds, e.g. dyes or fluorescent indicators, that are sensitive to the presence of a certain ion. As an illustrative example, a calcium sensitive fluorescent indicators such as fura-2, fluo-3, indo-1, BCECF, calcein may be included in the interior of the vesicle. As two further examples, a sodium sensitive indicator such as sodium-binding benzofuran isophthalate or corona green, or a potassium sensitive indicator such as potassium-binding benzofuran isophthalate may be included in the interior of the polymeric vesicle. A further illustrative example of an indicator that may be included in an aqueous solution is an indicator of redox potential, such as a redox sensitive dye, for example, hexamethylpararosaniline chloride (crystal violet).

In some embodiments, the presence of quantum dots or dyes in the interior of the polymeric vesicle may serve or assist in monitoring the integrity of the polymeric vesicles. Therefore, it is possible to instantaneously monitor whether the polymeric vesicle is intact, for example, during an in-vitro synthesis process. In some embodiments, a pharmaceutically active compound is included in the polymeric vesicle. If a channel protein, a transporter protein or a receptor channel is integrated into the membrane of the polymeric vesicle, a change in conditions of the ambience of the polymeric vesicle may cause the opening of the channel or activation of the transporter and thereby trigger the release of the pharmaceutically active compound. Such an embodiment may, for example, be used in vivo, such as in embodiments where the present system is transferred into an organism, such as a human or animal body.

The interior of the polymeric vesicle may also include a sample. Such a sample may be of any origin. It may for instance, but not limited to, be derived from humans, animals, plants, bacteria, viruses, spores, fungi, or protozoae, or from organic or inorganic materials of synthetic or biological origin. Accordingly, any of the following samples selected from, but not limited to, the group consisting of a soil sample, an air sample, an environmental sample, a cell culture sample, a bone marrow sample, a rainfall sample, a fallout sample, a sewage sample, a ground water sample, an abrasion sample, an archaeological sample, a food sample, a blood sample, a serum sample, a plasma sample, an urine sample, a stool sample, a semen sample, a lymphatic fluid sample, a cerebrospinal fluid sample, a nasopharyngeal wash sample, a sputum sample, a mouth swab sample, a throat swab sample, a nasal swab sample, a bronchoalveolar lavage sample, a bronchial secretion sample, a milk sample, an amniotic fluid sample, a biopsy sample, a cancer sample, a tumour sample, a tissue sample, a cell sample, a cell culture sample, a cell lysate sample, a virus culture sample, a nail sample, a hair sample, a skin sample, a forensic sample, an infection sample, a nosocomial infection sample, a production sample, a drug preparation sample, a biological molecule production sample, a protein preparation sample, a lipid preparation sample, a carbohydrate preparation sample, a space sample, an extraterrestrial sample or any combination thereof may be processed in the method. Where desired, a respective sample may have been preprocessed to any degree. As an illustrative example, a tissue sample may have been digested, homogenised or centrifuged prior to being used with the present system. The sample may furthermore have been prepared in form of a fluid, such as a solution. Examples include, but are not limited to, a solution or a slurry of a nucleotide, a polynucleotide, a nucleic acid, a peptide, a polypeptide, an amino acid, a protein, a synthetic polymer, a biochemical composition, an organic chemical composition, an inorganic chemical composition, a metal, a lipid, a carbohydrate, a combinatory chemistry product, a drug candidate molecule, a drug molecule, a drug metabolite or of any combinations thereof. Further examples include, but are not limited to, a suspension of a metal, a suspension of metal alloy, and a solution of a metal ion or any combination thereof, as well as a suspension of a cell, a virus, a microorganism, a pathogen, a radioactive compound or of any combinations thereof. It is understood that a sample may furthermore include any combination of the aforementioned examples.

The interior of the polymeric vesicle and the circumferential membrane define two immiscible phases, an outer phase, the membrane, and an inner phase, the interior of the vesicle. The outer phase is immiscible with the inner phase. Typically, the fluid of the outer phase is immiscible with the fluid of the inner phase. Often liquids are classified into polar and non-polar liquids in order to characterize properties such as solubility and miscibility with other liquids. Polar liquids typically contain molecules with an uneven distribution of electron density. The polarity of a molecule is reflected by its dielectric constant or its dipole moment. Polar molecules are typically further classified into protic and non-protic (or aprotic) molecules. A fluid, e.g. a liquid, that contains to a large extent polar protic molecules may therefore be termed a polar protic fluid. A fluid, e.g. a liquid, that contains to a large extent polar non-protic molecules may be termed a polar non-protic fluid. Protic molecules contain a hydrogen atom which may be an acidic hydrogen when the molecule is dissolved for instance in water or an alcohol. Aprotic molecules do not contain such hydrogen atoms.

Examples of non-polar liquids include, but are not limited to, hexane, heptane, cyclohexane, benzene, toluene, dichloromethane, carbon tetrachloride, carbon disulfide, dioxane, diethyl ether, or diisopropylether. Examples of dipolar aprotic liquids are methyl ethyl ketone, chloroform, tetrahydrofuran, ethylene glycol monobutyl ether, pyridine, methyl isobutyl ketone, acetone, cyclohexanone, ethyl acetate, isobutyl isobutyrate, ethylene glycol diacetate, dimethylformamide, acetonitrile, N,N-dimethyl acetamide, nitromethane, acetonitrile, N-methylpyrrolidone, methanol, ethanol, propanol, isopropanol, butanol, N,N-diisopropylethylamine, and dimethylsulfoxide. Examples of polar protic liquids are water, methanol, isopropanol, tert.-butyl alcohol, formic acid, hydrochloric acid, sulfuric acid, acetic acid, trifluoroacetic acid, dimethylarsinic acid [$(CH_3)_2AsO(OH)$], acetonitrile, phenol or chlorophenol. Ionic liquids typically have an organic cation and an anion that may be either organic or inorganic. The polarity of ionic liquids is known to be largely determined by the associated anion. While e.g. halides, pseudohalides, $BF_4^-$, methyl sulphate, $NO_3^-$, or $ClO_4^-$ are polar liquids, hexafluorophosphates, $AsF_6^-$, bis(perfluoroalkyl)-imides, and $[C_4F_6SO_3]^-$ are non-polar liquids.

The membrane of the polymeric vesicle is defined by one or more amphiphilic polymers, which can be the same or different. The term amphiphilic refers to a compound that is soluble in both polar and non-polar fluids. It also encompasses multiphase compounds. The amphiphilic properties of the polymer are due to the presence of both polar and non-polar moieties within the same molecule. In this regard, the polymer may be of surfactant nature. Accordingly, the polar properties of the polymer are based on a polar moiety. Two examples of such a moiety are a —COOH side group, in particular in the form of a charged COO⁻ group and an $SO_4H$ group, in particular in the form of an $SO_4^-$ group. Generally, a surfactant molecule includes a polar, typically hydrophilic, headgroup attached to a non-polar, typically hydrocarbon, moiety. Non-polar moieties of a polymer include a hydrocarbon chain that does not carry a functional group.

A polymer included in the circumferential membrane can be a synthetic polymer, a naturally occurring polymer or a combination thereof. As used herein the term "synthetic polymer" refers to polymers that are not found in nature, including polymers that are made from naturally occurring biomaterials. The use of an amphiphilic polymer allows choosing a polymeric vesicle of robust nature, i.e. with particularly high stability in terms of storage, resistance to shear forces and mechanical resistance, for instance in a screening assay. Polymeric vesicles such as block copolymeric vesicles (also termed 'polymersomes') have superior mechanical and physical properties compared to lipid-based vesicles (also termed liposomes). Polymeric vesicles can for instance typically be exposed to one magnitude higher critical areal strain before rupture compared to lipid vesicles. Therefore, high stability of membrane proteins incorporated can be provided against mechanical, chemical and microbial attacks. This allows a process-compatibility needed for industrial applications. Such polymeric vesicles can be easily stored and transported. Thus, in various embodiments, vesicles of the membrane protein carrier may be polymeric. In alternative embodiments, the membrane protein carrier comprises or consists of non-polymer based vesicles such as lipids and surfactants.

The membrane of the polymeric vesicle may include a plurality of amphiphilic polymers, including a plurality of block copolymers. An amphiphilic polymer included in the membrane of the vesicle may, for example, include a monomer unit of a carboxylic acid, an amide, an amine, an alkylene, a dialkylsiloxane, an ether and an alkylene sulphide. In some embodiments, it may include a polycarboxylic acid, a polyamide, a polyamine, a polyalkylene, a poly(dialkylsiloxane), a polyether, a poly(alkylene sulphide), and any combination thereof. In some embodiments, the amphiphilic polymer is a block copolymer. Any of the aforementioned examples of polymers may also define a block in a respective block copolymer. A variety of amphiphilic block copolymers is, for example, known in the art that undergo self-assembly in aqueous solution, thereby minimizing energetically unfavourable hydrophobe-water interactions. Some of these polymers are stimulus-responsive block copolymers. Any of these polymers can be used to define a circumferential membrane of a polymeric vesicle in the present system. It is noted in this regard that also amphiphilic homopolymers are known in the art that can undergo self-assembly into stable vesicles.

The amphiphilic polymer may for example be a diblock (A-B) or a triblock copolymer (A-B-A or A-B-C). In some embodiments, the amphiphilic polymer includes a polyether block such as an oligo(oxyethylene) block, a poly(oxyethylene) block, an oligo(oxypropylene) block, a poly(oxypropylene) block, an oligo(oxybutylene) block and a poly(oxybutylene) block. Further examples of blocks that may be included in the polymer include, but are not limited to, poly(acrylic acid), poly(methyl acrylate), polystyrene, poly(butadiene), poly(2-methyloxazoline), poly(dimethyl siloxane), poly(e-caprolactone), poly(propylene sulphide), poly(N-isopropylacrylamide), poly(2-vinylpyridine), poly(2-(diethylamino)ethylmethacrylate), poly(2-(diisopropylamino)ethylmethacrylate), poly(2-(methacryloyloxy)ethylphosphorylcholine) and poly(lactic acid). Examples of a suitable amphiphilic polymer include, but are not limited to, poly(ethyl ethylene)-b-poly(ethylene oxide) (PEE-b-PEO), poly(butadiene)-b-poly(ethylene oxide) (PBD-b-PEO), poly(styrene)-b-poly(acrylic acid) (PS-PAA), poly(2-methyloxazoline)-b-poly(di-methylsiloxane)-b-poly(2-methyloxazoline)(PMOXA-b-PDMS-b-PMOXA), poly(2-methyloxazoline)-b-poly(dimethylsiloxane)-b-poly(ethylene oxide) (PMOXA-b-PDMS-b-PEO), poly(ethylene oxide)-b-poly(propylene sulfide)-b-poly(ethylene oxide) (PEO-b-PPS-b-PEO) and apoly(ethylene oxide)-poly(buylene oxide) block copolymer. A block copolymer can be further specified by the average block length of the respective blocks included in a copolymer. Thus $PB_M PEO_N$ indicates the presence of polybutadiene blocks (PB) with a length of M and polyethyleneoxide (PEO) blocks with a length of N. M and N are independently selected integers, which may for example be selected in the range from about 6 to about 60. Thus $PB_{35}PEO_{18}$ indicates the presence of polybutadiene blocks with an average length of 35 and of polyethyleneoxide blocks with an average length of 18. Likewise, $PB_{10}PEO_{24}$ indicates the presence of polybutadiene blocks with an average length of 10 and of polyethyleneoxide blocks with an average length of 24. As a further example, $E_O B_P$ indicates the presence of ethylene blocks (E) with a length of O and butylene blocks (B) with a length of P. O and P are independently selected integers, e.g. in the range from about 10 to about 120. Thus $E_{16}B_{22}$ indicates the presence of ethylene blocks with an average length of 16 and of butylene blocks with an average length of 22.

Depending on the polymer used, the membrane may assemble into various vesicle morphologies. Where block copolymers are included in the membrane, segregation of block copolymers may occur. In any such morphology, non-polar and thus hydrophobic portions of polymer molecules are typically located within the membrane rather than at the face thereof; they may bridge the membrane. Polar portions of the polymer may be arranged at the interface with the medium in which the polymeric vesicle is included, e.g. an aqueous medium. AB diblock copolymers can for example form an interdigitated symmetric membrane. A binary mixture of AB and BC diblock copolymers can result in a morphology of at least partially spatial segregation of AB and BC blocks within the membrane. Likewise, ABC triblock copolymers can form amorphology of at least partially spatial segregation.

A suitable polyether may for example include one of an oligo(oxyethylene) block or segment, a poly(oxyethylene) block (or segment), an oligo(oxypropylene) block, a poly(oxypropylene) block, an oligo(oxybutylene) block and a poly(oxybutylene) block. An illustrative example of a respective triblock copolymer is a poloaxamer. A poloaxamer is a difunctional block copolymer surfactant terminating in primary hydroxy groups. It typically has a central non-polar chain, for example, of poly-oxypropylene (poly(propylene oxide)), flanked by two hydrophilic chains of e.g. poly-oxyethylene (poly(ethylene oxide)). The polyether may thus in some embodiments be a poly(ethylene oxide)-poly(propylene oxide)-poly(ethylene oxide) (PEO-PPO-PEO) triblock copolymer. The lengths of the polymer blocks can be customized, so that a large variety of different poloxamers with slightly different properties is commercially available. For the generic term "poloxamer", these copolymers are commonly named with the letter "P" (for poloxamer) followed by three digits, the first two digits multiplied by 100 give the approximate molecular mass of the polyoxypropylene core, and the last digit multiplied by 10 gives the percentage polyoxyethylene content (e.g., P407=Poloxamer with a polyoxypropylene molecular mass of 4,000 g/mol and a 70% polyoxyethylene content). For the Pluronic tradename, coding of these copolymers starts with a letter to define it's physical form at room temperature (L=liquid, P=paste, F=flake (solid)) followed by two or three digits, the first digit(s) refer to the molecular mass of the polyoxypropylene core (determined from BASF's Pluronic grid) and the last digit multiplied by 10 gives the percentage polyoxyethylene content (e.g., F127=Pluronic with a polyoxypropylene molecular mass of 4,000 g/mol and a 70% polyoxyethylene content). The polyether may for example be a triblock copolymer of oxirane with 2-methyl-oxirane, having the Chemical Abstract No. 691397-13-4. Illustrative examples of such a polyether are the commercially available triblock copolymers Adeka Pluronic F 68, Nissan Plonon 104, Novanik 600/50, Lutrol 127, Pluriol PE 1600, Plonon 104, Plonon 407, Pluronic 103, Pluronic 123, Pluronic 127, Pluronic A 3, Pluronic F-127, Pluronic F 168, Pluronic 17R2, Pluronic P 38, Pluronic P 75, Pluronic PE 103, Pluronic L 45, Pluronic SF 68, Slovanik 310, Synperonic P 94 or Synperonic PE-F 127, to name a few.

The amphiphilic polymer included in the circumferential membrane of the polymeric vesicle may in some embodiments have a glass transition (Tg) temperature at standard atmospheric pressure that is below ambient temperature, e.g. below about 22° C. If the temperature of a polymer is decreased, the glass transition temperature corresponds to the temperature at which amorphous domains of a polymer take glass style characteristics in terms of rigidity, stiffness and rigidity. The glass transition temperature may for example be selected below about 0° C., such as below about −40° C., e.g. below about −60° C., below about −80° C. or below about −90° C., such as for instance about −93° C., about −100° C., about −125° C. or about −130° C.

In some embodiments, a polymer included in the circumferential membrane of the polymeric vesicle is biocompatible, including pharmaceutically acceptable. An illustrative example of a respective block is poly(D,L-lactide-co-glycolide), for example included in the polymer pluronic-poly (D,L-lactide-co-glycolide). The term "biocompatible" (which also can be referred to as "tissue compatible"), as used herein, is a polymer or polymer block that produces little if any adverse biological response when used in vivo. The term thus generally refers to the inability of such a block or polymer to promote a measurably adverse biological response in a cell, including in the body of an animal, including a human. A biocompatible polymer block or polymer can have one or more of the following properties: non-toxic, non-mutagenic, non-allergenic, non-carcinogenic, and/or non-irritating. A biocompatible polymer block or polymer, in the least, can be innocuous and tolerated by the respective cell and/or body. A biocompatible polymer block or polymer, by itself, may also improve one or more functions in the body.

Examples of suitable biocompatible polymer blocks include non-absorbable polymer blocks such as polypropylene, polyethylene, poly(ethylene terephthalate), poly(butylene terephthalate), polytetrafluoroethylene, polyaryletherketone, nylon, fluorinated ethylene propylene, polybutester, and silicone; absorbable polymer blocks such as polyglycolic acid (PGA), polylactic acid (PLA), polycaprolactone, and polyhydroxyalkanoate.

In alternative embodiments, the membrane protein carrier may comprise or consist of a polymeric planar structure. The polymeric planar structure may have a planar membrane comprised of the same or different amphiphilic block copolymer. Planar membranes may be formed on support surfaces via polymerization, grafting or spreading.

Discussions with respect to the nature and types of polymers suitable for use as the polymeric vesicles apply generally to the polymeric planar structures as well. Hence, to facilitate the illustration and understanding of the present discussion, the present discussion will focus on the membrane protein carrier being comprised or consisted of a polymeric vesicle. Therefore, it is to be understood and appreciated that references to a membrane protein carrier comprising or consisting of a polymeric vesicle may also refer to a membrane protein carrier comprising or consisting of a polymeric planar structure.

In various embodiments, the at least one membrane protein is associated with the at least one membrane protein carrier by associating with the circumferential membrane of the amphiphilic block copolymer of the polymeric vesicle of the membrane protein carrier. The resultant membrane protein carrier in such embodiments may also be termed a proteopolymersome or artificial cell membrane. In exemplary embodiments, the membrane protein is associated with by embedding, integrating, or inserting into the circumferential membrane of the polymeric vesicle. The membrane protein associated with, embedded, integrated, or inserted into the circumferential membrane of the polymeric vesicle may be any membrane protein, as defined above. By embedding, integrating, or inserting the membrane protein into the circumferential membrane of the polymeric vesicle is meant that the membrane protein is found, in part or in whole, in the circumferential membrane of the polymeric vesicle. A portion of the membrane protein may be embedded, integrated, or inserted into the circumferential membrane of the polymeric vesicle. The embedded, integrated, or inserted portion may be a major portion (i.e. more than half) of the membrane protein or a minor portion (i.e. less than half) of the membrane protein. Alternatively, the entire membrane protein may be embedded, integrated, or inserted into the circumferential membrane of the polymeric vesicle. In alternative embodiments, the membrane protein is associated with by attaching onto the circumferential membrane of the polymeric vesicle. By attaching the membrane protein onto the circumferential membrane of the polymeric vesicle is meant that the membrane protein is found at the periphery of the circumferential membrane of the polymeric vesicle.

In various embodiments, embedding, integrating, or inserting a portion of the membrane protein includes reconstitution, insertion, or spontaneous insertion via in vitro synthesis of the membrane protein in the circumferential membrane of the amphiphilic block copolymer of the polymeric vesicle. The membrane proteins do not necessarily have to be from in vitro, it may also be isolated from its natural membranes and can be integrated by reconstitution while making vesicles or spontaneous insertion into preformed polymeric vesicles.

In various embodiments, the membrane protein may be associated, including, where applicable, integrated into the circumferential membrane by means of a cell-free expression system. Such a cell-free expression system allows a nucleic acid encoding the selected membrane protein to be transcribed and translated, for example. Therefore, the membrane protein is formed in situ and immediately incorporated into the circumferential membrane. Such a cell-free expression system is typically an in vitro transcription and translation system. In some embodiments, an eukaryotic cell-free extract is used as an expression system. Suitable expression systems are commercially available, e.g. as TNT® coupled transcription/translation system by Promega. In some embodiments, a prokaryotic cell-free expression system (e.g. RTS 100 *E. coli* by Kit™ by Roche Applied Science) or an archaic cell-free expression system is used.

The term "nucleic acid molecule" as used herein refers to any nucleic acid in any possible configuration, such as single stranded, double stranded or a combination thereof. Nucleic acids include, for instance, DNA molecules, RNA molecules, analogues of the DNA or RNA generated using nucleotide analogues or using nucleic acid chemistry, locked nucleic acid molecules (LNA), PNA molecules, and tecto-RNA molecules. A PNA molecule is a synthetic nucleic acid analogue with a pseudopeptide backbone in which the phosphodiester backbone present in, for example, DNA or RNA is replaced by repetitive units of short aliphatic moieties with an amino end and a carboxylic end, forming an amide bond in the oligomer or polymer. An LNA molecule has a modified RNA backbone with a methylene bridge between C4' and O2', which locks the furanose ring in a N-type configuration, providing the respective molecule with a higher duplex stability and nuclease resistance. Unlike a PNA molecule, an LNA molecule has a charged backbone. DNA or RNA may be of genomic or synthetic origin and may be single or double stranded. Such nucleic acid can be, for example, mRNA, cRNA, synthetic RNA, genomic DNA, cDNA synthetic DNA, a copolymer of DNA and RNA, oligonucleotides. A respective nucleic acid may furthermore contain non-natural nucleotide analogues and/or be linked to an affinity tag or a label.

The association of a membrane protein with the circumferential membrane, including its integration/insertion therein, can be monitored using any suitable detection method available in the art. As an illustrative example, it may be monitored in real-time by surface plasmon resonance spectroscopy, which may be applied in combination with surface plasmon enhanced fluorescence spectroscopy. Thus, in one aspect, use of an artificial cell membrane system of the first aspect as a reagent in a fluorescence, chemi-luminescence, or radioactivity detection technique is provided. In various embodiments, the membrane protein carrier further includes a fluorescent dye, metal, chemical, or radioactive substance for such detection purposes. For example, the artificial cell membrane may be used in scintillation proximity assay, a filter plate assay or flow cytometry. In further exemplary embodiments, the artificial cell membrane may be used in detection techniques for applications in drug, ligand, or antibody screening, or in functional assays for membrane proteins.

In some embodiments, the membrane protein is associated with or integrated into the circumferential membrane of the vesicle that is intended to be subject to an assay or a screening method. As an example, it may be desired to identify a compound that is capable of modulating, such as stimulating or inhibiting, including blocking, a membrane protein. The respective membrane protein, which may be any membrane protein, may be expressed and associated with or integrated into the circumferential membrane of the polymeric vesicle of the present system. Where a measurable effect of the membrane protein, e.g. a cellular response, is known the required components to achieve such a response may be integrated into the polymericvesicle. In embodiments where the membrane protein is responsive to external molecules, it may be termed a receptor protein. A respective molecule from the ambience may form a complex with the receptor protein. Therefore, the receptor protein may undergo a change, such as a conformational change, from an active state to an inactive state and vice versa. As a first step, it may be desired to identify a compound that is able to form a complex with such a receptor protein. Once such a complex is identified a cellular effect may be analysed, for example, by expressing an effector protein and integrating the same into the polymeric vesicle. A stimulation or inhibition of the effector protein may then be determined. In various embodiments, the analyte molecule binds specifically to a membrane protein associated with a membrane protein carrier of the artificial cell membrane system. The analyte molecule to be detected may be, but is not limited to, a cell, protein, peptide, nucleotide, or ligand.

The solid support is freely suspended in a fluid medium. By freely suspended or free-floating, both terms used interchangeably, is meant that the solid support is not bound to a surface of the container containing the suspension, i.e. a gap exists between the surface of the container and the solid support, and movement of the solid support is therefore not restricted. In other words, the fluid medium contains a solid support of lower, equal, or higher density which may be floating at a position away from the surface of the container upon gentle agitation. For example, the solid support is located at a surface of the fluid medium open to the environment. In another example where the fluid medium consists of a lower dense fluid and an upper less dense fluid, the solid support can be located in the lower dense fluid, or located in the upper less dense fluid, or located at the interface between the two fluids, depending on the respective density of the solid support, lower dense fluid, and upper less dense fluid. In certain embodiments, the solid supports are denser than the liquid medium, which may be water, PBS buffer or a cell culture medium, for example. Upon gentle agitation, the solid supports can be free-floating, i.e. being not bound to a surface of the container, for a period of time.

A membrane protein carrier is nevertheless attached to a surface of the solid support. In various embodiments, the membrane protein carrier is attached to the surface of the solid support via physisorption. In further various embodiments, the membrane protein carrier is attached to the surface of the solid support via chemisorption. The attachment mechanism may be provided by, but is not limited to, covalent bonding, non-covalent interactions such as Van der Waals interaction, hydrogen bonding, hydrophobic interaction, solvation force, electrostatic interaction, or Casimir interaction. In various embodiments, the at least one membrane protein carrier, or the solid support, or both the membrane protein carrier and the solid support, include a functional group facilitating attachment to each other. The functional group may be, but is not limited to, an imino, amino, mercapto, or carboxylic acid group. Other suitable binding compounds may include streptavidin-biotin and functional groups involving click chemistry for conjugation, such as actylenes and azides.

The solid support may be made of any material, such as but not limited to, a polymer, metal, organic, inorganic, or a mixture thereof. In various embodiments, the solid support has at least a three-dimensional shape, such as a three-dimensional shape or a four-dimensional shape. In embodiments where the solid support has a three-dimensional shape, the three-dimensional shape may include, but is not limited to, a sphere, box, cylinder, cone, wedge, pyramid, and torus. In certain embodiments, the solid support is spherical. The solidsupport can be a microsphere or a nanosphere, depending on the physical dimension of the solid support. In various embodiments, the solid support may have a mean diameter of about 1 nm to about 10 mm. For example, the diameter of the microsphere is in the range of about 1 to about 500 µm (i.e. microns), such as about 1 µm, about 5 µm, about 10 µm, about 20 µm, about 25 µm, about 50 µm, about 100 µm, about 150 µm, about 200 µm, about 250 µm, about 300 µm, about 350 µm, about 400 µm, about 450 µm, or about 500 µm. The diameter of the nanosphere may be in the range from about 1 nm to about 1 µm, such as about 1 nm, about 5 nm, about 10 nm, or about 50 nm, about 100 nm, about 500 nm, or about 900 nm. The nanosphere may be a quantum dot, gold nanoparticle, or other nanoparticle. Solid supports having a mean diameter up to 10 mm, such as agarose or glass beads, may also be useful. In one embodiment, the solid support is a microsphere, also termed a microbead, or simply, termed a bead if the solid support is spherical. In such embodiments, the membrane protein carrier (prior to the association with a membrane protein) attached to the surface of the bead may be termed a vesicle-bead. Correspondingly, a membrane protein carrier associated with a membrane protein or a plurality of membrane proteins and attached to the surface of the bead may be termed a proteopolymersome-bead. In various embodiments, the solid support comprises or consists of a polymer, a metal, an inorganic compound, an organic compound, a fluorescent substance, or a radioactive substance.

In various embodiments, the solid support is bigger in size than the at least one membrane protein carrier. The bigger sized solid support allows accommodation of attachment of more than one membrane protein carrier. Thus, in certain embodiments, the artificial cell membrane system comprises one or more solid supports and a plurality of membrane protein carriers is attached to each solid support. For example, the mean diameter of the solid support is larger than the mean diameter of the membrane protein carrier. The term "diameter" as used herein refers to the maximal length of a straight line segment passing through the center of a figure and terminating at the periphery. Accordingly, the term "mean diameter" refers to an average diameter of the solid support or the membrane protein carrier, and may be calculated by dividing the sum of the diameter of each solid support or membrane protein carrier by the total number of solid supports or the membrane protein carriers, respectively. Although the term "diameter" is used normally to refer to the maximal length of a line segment passing through the centre and connecting two points on the periphery of a sphere, it is also used herein to refer to the maximal length of a line segment passing through the centre and connecting two points on the periphery of other shapes. In various embodiments, the mean diameter of the membrane protein carriers is less than about 500 nm, such as 400 nm, 300 nm, 200 nm, 100 nm, 50 nm, or 10 nm. For example, the membrane protein carriers may be attached or otherwise conjugated to nanometer-sized particles such as gold nanoparticles or quantum dots via biotin-streptavidin or thiols. In various embodiments, each solid support carries at least 10, or at least 100, or at least 1,000 membrane protein carriers. The number of membrane protein carriers attached to the solid support is limited by the availability of the surface area on the solid support and the size/diameter of the membrane protein carriers. For example, 10,000 membrane protein carriers with a mean diameter of 100 nm may cover the surface of one 5 μm spherical solid support whereas only 100 carriers of 100 nm diameter can over the surface of one 500 nm spherical solid support. In yet certain embodiments, the solid support is smaller in size than the at least one membrane protein carrier such that a plurality of solid supports may be attached to the at least one membrane protein carrier.

The shape of the solid support can also be less than three-dimension, such as a planar surface. However, a three-dimensional shape, particularly spherical but not necessarily so, is preferred since it presents a more homogenous distribution as well as a higher surface density of attached membrane proteins than a planar surface, for example. Further, the handling, storage and manipulation of large three-dimensional solid supports attached with membrane protein carriers are far easier than similar efforts involving individual membrane protein carriers of approximately 100 nm each. Thus, while described herein for illustration is directed to an artificial cell membrane system comprising a solid support and at least one membrane protein carrier associated with a membrane protein, it is to be appreciated that the present artificial cell membrane system can similarly comprise a plurality of membrane protein carriers, a plurality of associated membrane proteins, a plurality of solid supports, or a combination thereof. For example, the present artificial cell membrane system includes, but is not limited to, a plurality of membrane protein carriers (can be the same type or different) each associated with a single or multiple membrane proteins (can be the same type or different), and the plurality of the membrane protein carriers are attached to a surface of a single solid support. Other configurations on the number and types of solid support, membrane protein carrier, and membrane protein are also possible.

A membrane protein may be associated with a membrane protein carrier either prior to the attachment of the membrane protein carrier to a surface of a solid support (FIG. 1(A)) or after the attachment of the membrane protein carrier to a surface of a solid support (FIG. 1(B)). The membrane protein may be associated with the membrane protein carrier prior to the step of adding the membrane protein carrier to the fluid medium so that the membrane protein carrier associated with the membrane protein is attached to the surface of the solid support. Alternatively, the membrane protein may be associated with the membrane protein carrier after the step of incubating the fluid medium containing the suspension of the solid support and the membrane protein carrier so that the membrane protein carrier is attached to the surface of the solid support first, followed by the association step. Attaching carriers onto solid support prior to the association of carriers with membrane proteins allows the assessment of the same membrane proteins in response to different types of membrane protein carriers. For example, different carriers/vesicles can be attached onto the surface of encoded solid supports and carrier-attached solid supports can be pooled together for the association of membrane proteins in one reaction. Attaching carriers onto solid support after the association of the membrane proteins allows a more uniform membrane protein association reaction as solid supports are not involved until the completion of the membrane protein association reaction. Also, membrane protein carriers containing membrane proteins can be prepared in excess if attachment onto the solid support is carried out afterwards. This allows other studies on the membrane proteins in their carriers parallel to the study on their carriers on solid support.

In certain embodiments, a membrane protein carrier is added to a fluid medium containing a suspension of a freely suspended solid support. In other embodiments, a fluid medium containing a suspension of a freely suspended solid support is added to a membrane protein carrier. In yet further embodiments, a membrane protein carrier and a fluid medium containing a suspension of a freely suspended solid support are simultaneously added to a container. In other words, the order of addition of one component to another component is immaterial. Thus, the step of adding the membrane protein carrier to the fluid medium containing the suspension of the freely suspended solid support includes any one of the above scenario.

Any suitable fluid medium may be used for suspending the solid support so long as the resultant suspension contains a freely suspended solid support. As described above, the fluid medium may have lower, equal, or higher density than the solid support. The fluid medium may include a homogeneous phase or a non-homogeneous phase where an upper less dense phase and a lower dense phase exist. The fluid medium may be an aqueous solution or otherwise. In one embodiment, the fluid medium is water.

To facilitate the attachment of a membrane protein carrier to a surface of a freely suspended solid support, the fluid medium containing the suspension of the freely suspended solid support and the membrane protein carrier is incubated. The parameters for incubating the fluid medium (for example, temperature, incubation time and pressure) can be readily determined by a person of average skill in the art. For example, the incubation time can be about 1 h, about 6 h, about 12 h, about 18 h, about 24 h, or more. The fluid medium may be incubated at ambient temperature, for example. During incubating, the fluid medium may be subjected to vortexing, such as 1,000 rpm vortexing.

In conclusion, membrane protein carriers (also termed artificial cell membranes) associated with membrane proteins attached to freely suspended solid supports, such as microbeads, have been disclosed. Such beads with artificial cell membranes are produced by the unique combination of several different procedures: bead surface chemistry, block copolymer chemistry, conjugation methods and cell-free methods. The free-floating solid support membrane protein carriers can be easily produced via different procedures as illustrated. Polymeric vesicles made of self-assembled block copolymers are attached onto the free-floating solid supports through either physisorption or chemisorption. Membrane proteins can be integrated into the membranes of the polymeric vesicles on the solid supports via reconstitution, insertion or spontaneous insertion via in vitro synthesis. The as-obtained artificial cell membranes or proteopolymersomes can be exploited for applications as they are now carried by the free-floating solid supports because of its relatively large surface area. With the present artificial cell membrane system, any given membrane protein more or less in pure and correctly folded form concentrated on free-floating solid support that can be used for analytical studies can be generated. Technologies based on flow cytometry (for example, beads) can be readily applied. The present artificial cell membrane system may find various applications in drug design and discovery, drug screening assays, antibody production, drug delivery, membrane protein production, or antibody screening methods.

In order that the invention may be readily understood and put into practical effect, particular embodiments will now be described by way of the following non-limiting examples.

EXAMPLES

Example 1

In the examples illustrated below, microbeads were used as an illustrative embodiment of a free-floating 3D solid support for the attachment of polymeric vesicles as artificial cell membranes. Polymeric vesicles were attached onto microbeads (vesicle-beads) through physisorption. Fluorescence microscope and scanning electron microscope (SEM) imaging were used to characterize the vesicle-beads. The pore-forming protein α-hemolysin (α-HL) and the immunologically important protein major histocompatibility complex class I (MHC-I) were chosen as membrane protein models. By incubating vesicle-beads with α-HL molecules, these membrane proteins were reconstituted in the vesicle membranes as pores. Subsequent experiments were undertaken to study the release of components, such as calcein which had already been encapsulated inside the vesicles, through the pores. On the other hand, MHC-I proteopolymersomes on microbeads were obtained by in vitro synthesis, where MHC-I proteins were expressed in the presence of vesicle-beads by mixing MHC-I cDNA, vesicle-beads and the in vitro synthesis master mix together. The presence and the conformational folding of the integrated MHC-I proteins were demonstrated by staining the MHC-I proteopolymersomes on microbeads with anti-His antibodies and conformational anti-H-2Kb-OVA antibodies, respectively. As the submicrometer sized artificial cell membranes were immobilized on micrometer sized beads, signal detection could be carried out on the ubiquitous fluorescence microscope.

Materials and Methods

Preparation of Vesicle-Beads

Polymeric vesicles were prepared using the triblock copolymer poly(2-methyloxazoline)$_{20}$-block-poly(dimethylsiloxane)$_{54}$-Nock-poly(2-methyloxazoline)$_{20}$ (ABA) according to a method detailed elsewhere (such as described in Nardin et al., *Langmuir* (2000), 16(3):1035-1041). ABA vesicles with membrane-staining dye Rhodamine B octadecyl ester perchlorate (RBOE), or ABA-RBOE vesicles for short, were obtained by adding 1 mol % RBOE during vesicle preparation. ABA-RBOE vesicles loaded with calcein at self-quenching concentration in the interior space, i.e. calcein-ABA-RBOE vesicles for short, were prepared by rehydrating the dry polymer thin film with 30 mM calcein in 1×PBS buffer. ABA-RBOE vesicles and calcein-ABA-RBOE vesicles were prepared at a final concentration of about 20 mg/ml and 5 mg/ml, respectively. Non-encapsulated calcein molecules were removed by dialysis.

SuperAvidin™ coated polystyrene microspheres (PS-SA) with a mean diameter of 5.6 μm (1 wt % solid) were washed three times using Wash Solution (0.01 wt % bovine serum albumin (BSA) in MilliQ water), then re-suspended in MilliQ to obtain the original concentration. ABA-RBOE vesicles and PS-SA beads were mixed at a volume ratio of 1:1 while calcein-ABA-RBOE vesicles and PS-SA beads were mixed at a volume ratio of 4:1. They were incubated overnight with 1,000 rpm vortexing to allow the attachment of polymeric vesicles onto the microbeads. The as-obtained vesicle-beads, ABA-RBOE-PS-SA or calcein-ABA-RBOE-PS-SA, were washed three times using Wash Solution then re-suspended in MilliQ and adjusted to a final bead concentration of 1 wt %.

The ABA triblock copolymer was purchased from Polymer Source, Canada. The RBOE and calcein dyes were bought from Sigma, Singapore. PS-SA microbeads were purchased from Bangs Laboratories, USA.

Preparation of α-Hemolysin (α-HL) Proteopolymersome-Beads

Pore-forming membrane protein, α-HL was reconstituted into vesicle-beads by incubating vesicle-beads with α-HL (0.5 mg/mlin MOPS-NaCl buffer). α-HL from *Staphylococcus aureus* and MOPS powder for MOPS buffer were purchased from Sigma, Singapore.

Preparation of Major Histocompatibility Complex Class I (MHC-I) Proteopolymersome-Beads MHC-I proteopolymersome-beads were obtained via an overnight in vitro synthesis reaction containing 5 μl of 1 wt % vesicle-beads, 8 μl of 840 ng/μl MHC-I cDNA (MHC-I gene cloned into a plasmid vector), 30 μl of master mix from TNT® SP6 High-Yield Wheat Germ Protein Expression (Promega, Singapore) and 7 μl of nuclease-free water. The MHC-I cDNA was designed for the expression of MHC-I complexed with an OVA peptide according to an earlier study (such as described in Mitaksov et al., *Chemistry & Biology* (2007), 14(8):909-922) and the protein's C-terminus was tagged with a His-tag.

Characterization of Vesicle-Beads

An Olympus BX51 fluorescence microscope and a JEOL FESEM JSM6700F scanning electron microscope (SEM) were used to characterize the vesicle-beads. For fluorescence microscope imaging, the samples were diluted 3× in MilliQ water and 3 µl of ABA-RBOE-PS-SA vesicle-beads or bare PS-SA beads were dispensed and sandwiched between 2 glass coverslips. Fluorescence imaging of the vesicle-beads and the bare beads were carried out using the same excitation/emission filter set, exposure time and gain settings. For SEM imaging, 1 µl of ABA-RBOE-PS-SA vesicle-beads or bare PS-SA beads and 2 µl of water were dispensed onto a small piece of glass slide; the vesicle-beads or bare beads were allowed to settle down for 3 min and then samples were gently rinsed with distilled water and dried at room temperature. These samples were coated with a thin layer of gold (JFC-1200 coater, JEOL) for 30 sec at 10 mA before imaging.

Characterization of α-HL Proteopolymersome-Beads by Calcein Release Studies

For calcein release, vesicle-beads, calcein-ABA-RBOE-PS-SA beads were pelleted and re-suspended in MOPS-NaCl buffer at 0.1 wt %. α-HL proteopolymersome-beads were prepared by incubating the vesicle-beads with α-HL in MOPS-NaCl buffer and the reconstitution of α-HL were monitored by calcein release studies using either a Tecan Fluorescence plate reader or an Olympus BX51 fluorescence microscope. In a plate reader based study, samples were prepared in a Greiner 384 Flat Bottom Black Polystyrol microplate.

Firstly, four wells were each filled with 10 µl of calcein-ABA-RBOE-PS-SA vesicle-beads and 27 µl of MOPS buffer and another two wells were each filled with 37 µl of MOPS buffer. Four fluorescence reads were taken from each well every 10 min for 30 min using an excitation wavelength at 490±9 nm and an emission wavelength at 525±20 nm.

Subsequently, two of the four wells having vesicle-beads were each added with 10 µl of α-HL (0.5 mg/ml in MOPS buffer) to form the α-HL proteopolymersomes-beads and the other two wells were each added with 10 µl of MOPS buffer to serve as controls. Also, 10 µl of MOPS buffer were added into each of the two wells having only buffer for subtracting readings from buffer itself.

Fluorescence was then read every 10 min for 2 h. Calcein fluorescence intensity was calculated by subtracting the mean reading of the two buffer wells from the two vesicle-bead wells added with α-HL or MOPS buffers. The calcein fluorescence intensity as a function of time was plotted using OriginPro 8.5 for the comparison of calcein release from the α-HL proteopolymers on-beads with that from the vesicle-beads without incubation with α-HL.

For the fluorescence microscope based calcein release study, 1 µl of calcein-ABA-RBOE-PS-SA vesicle-beads and 2 µl of MOPS buffer were dispensed onto glass coverslip; vesicle-beads were allowed to settle down for 3 min and liquid was gently removed by using a piece of tissue. Samples were imaged before completely drying for both the green and the red emission for calcein and RBOE, respectively. Then 3 µl of α-HL was added onto the vesicle-beads. The sample was incubated for 3 min at room temperature in the dark and rinsed gently with MOPS buffer. Images were taken using the same filters, exposure time and gain for the comparison of the vesicle-beads before and after incubation with α-HL.

Characterization of MHC-I Proteopolymersome-Beads by Antibody Binding Studies

The presence and the folding of the in vitro expressed MHC-I membrane protein in the vesicle-beads were characterized by antibody binding tests using anti-His and the conformational anti-H-2Kb-OVA, respectively. For the antibody binding tests, the MHC-I proteopolymersome-beads were prepared as described above and a negative control was prepared using the same protocol but without adding the MHC-I cDNA.

After the in vitro synthesis, the vesicle-beads in the test sample and the control were pelleted down and 25 µl of the supernatant was taken out. The vesicle-beads were blocked by incubation with Blocking Buffer (2 wt % BSA in 1×PBS) for 2 h. After blocking, the vesicle-beads were pelleted down and 200 µl of the supernatant was discarded. The vesicle-beads in the test and control samples were resuspended in 150 µl Diluent Buffer (0.01 wt % BSA in 1×PBS). Fifty microliters of the vesicle-beads from the test and control samples were used for each antibody binding test.

Primary antibodies, mouse anti-His (anti-His Tag, clone HIS.H8, from Millipore) and anti-H-2Kb-OVA (anti-mouse OVA257-264 (SIINFEKL) peptide bound to H-2Kb Purified, from eBioscience) were freshly prepared in Diluent Buffer at 2 µg/ml and 1 µg/ml, respectively; and 200 µl of the primary antibodies were added into the vesicle-beads test and control samples. Incubation with the primary antibodies was carried out for 3.5 h. The vesicle-beads were pelleted down and 200 µl of the supernatant were discarded. The vesicle-beads were washed once with 200 µl of the Diluent Buffer.

Secondary antibody, anti-mouse labeled with Alexa Fluor® 488 (Alexa Fluor® 488 Goat Anti-Mouse IgG (H+L), from Invitrogen) was freshly prepared in Diluent Buffer at 4 µg/ml and 200 µl of the secondary antibody were added into the test and control samples. Incubation with secondary antibody was carried out for 1.5 h. Vesicle-beads was pelleted down and 200 µL of the supernatant were discarded. The vesicle-beads were washed twice, each time with 200 µl of the Diluent Buffer. After washing, the vesicle-beads were resuspended in 50 µl Diluent Buffer and prepared for imaging.

All incubation was carried out at room temperature with 1,000 rpm continuous vortexing; and for incubation with labeled antibody, it was carried out in a dark chamber. All pelleting of vesicle-beads was done by centrifugation at 4° C. for 10 min. Washing of the vesicle-beads was carried out as follows: resuspending the vesicle-beads in the Diluent Buffer by gently pipetting the dispersant up and down seven times, pelleting down the vesicle-beads and removing 200 µl of the supernatant. For imaging of the vesicle-beads using fluorescence microscope, 3 µl vesicle-beads were dispensed onto glass coverslip and covered with another piece of coverslip. All samples were imaged with the same imaging parameters: filter, exposure time and gain.

Results

Characterization of the Vesicle-Beads

Figure 2:
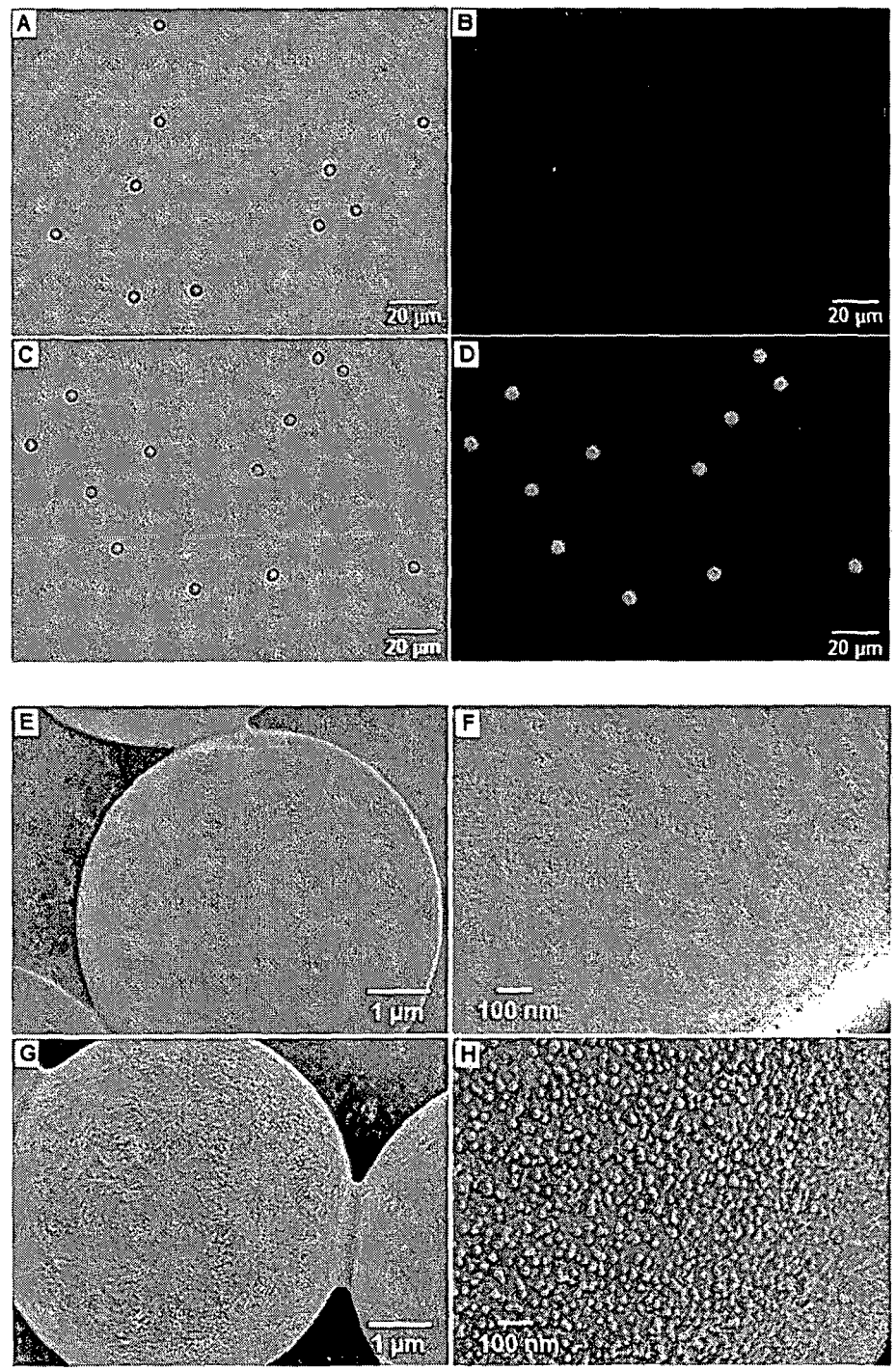
FIG. 2 shows polymeric vesicles attached on the 3D surfaces of microbeads, i.e. vesicle-beads (C), (D), (G), and (H) in comparison with bare microbeads without vesicle attachment (A), (B), (E), and (F) in accordance with the example described below. (A) and (C) relate to bright field optical micrographs; (B) and (D) relate to fluorescence optical micrographs. (E)-(H) relate to SEM images. Polymeric vesicles were loaded with membrane-staining amphiphilic dye. The attachment of vesicles on beads was demonstrated by the fluorescent beads in (D) and the bead surface decorated with polymeric vesicles in (G) and (H).

The attachment of the polymeric vesicles onto microbeads was confirmed by fluorescence microscope imaging and the surface morphology of the vesicle-beads was characterized by SEM imaging. ABA-RBOE-PS-SA vesicle-beads (the membrane of the vesicles was stained with RBOE dye) were imaged together with the PS-SA bare beads (without vesicle attachment) as a control and the images are shown in FIG. 2. Optical micrographs of the bare PS-SA beads in FIGS. 2A and 2B show that the bare PS-SA beads had no RBOE fluorescence whereas the ABA-RBOE-PS-SA vesicle-beads (FIGS. 2C and 2D) show strong RBOE fluorescence. FIGS.

2A-2D demonstrate that ABA-RBOE polymeric vesicles were successfully attached onto the PS-SA microbeads.

The surface morphology of the vesicle-beads as compared with that of the bare beads was viewed by SEM. The SEM images in FIGS. 2E-2H show that the surface of the bare PS-SA beads was smooth (FIGS. 2E and 2F) whereas the surface of the ABA-RBOE-PS-SA vesicle-beads was decorated with packed polymeric vesicles with an average diameter of about 30 nm (FIGS. 2G and 2H). This is in good agreement with the earlier reported size of polymersomes made of ABA block copolymers.

Characterization of α-HL Proteopolymersome-Beads by Calcein Release Studies

Figure 3:
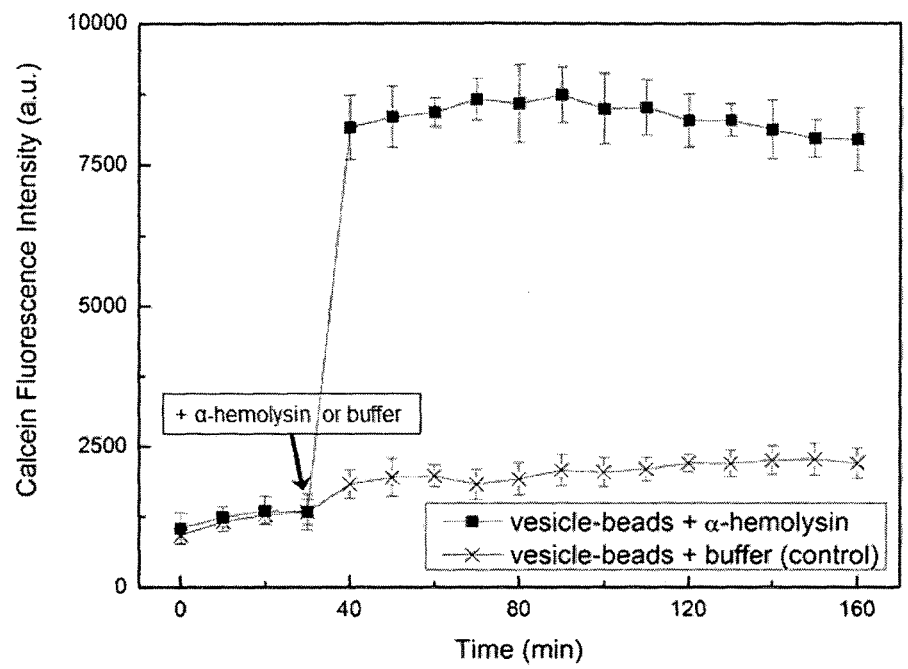
FIG. 3 shows calcein release from vesicle-beads incubated with α-hemolysin, showing calcein fluorescence intensity as a function of time for vesicle-beads incubated with α-hemolysin or buffer (control).

The formation of α-HL proteopolymersome-beads was monitored by calcein release in both plate reader and fluorescence microscope based studies. Results from the plate reader based study (FIG. 3) show an increase in calcein fluorescence intensity upon the addition of α-HL into the calcein-ABA-RBOE-PS-SA vesicle-beads. Calcein fluorescence intensity from the vesicle-beads incubated with α-HL was about 4.45 times that from the control sample (vesicle-beads incubated with buffer only). The increase in calcein intensity from the vesicle-bead suspension indicates the successful incorporation of α-HL protein or the formation of α-HL pores into the membranes of the vesicle-beads.

Figure 4:
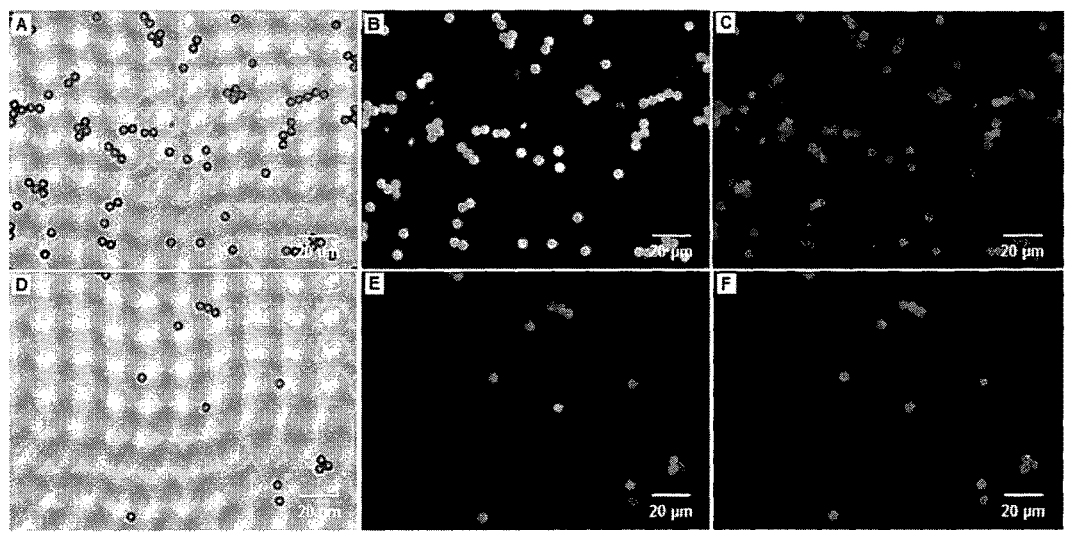
FIG. 4 shows calcein release from vesicle-beads incubated with α-hemolysin, showing optical micrographs of vesicle-beads (A)-(C) before and (D)-(F) after incubation with α-hemolysin and rinsing with buffer. Polymeric vesicles were loaded with a membrane-staining dye and 30 mM calcein in the interior space before attaching onto the beads. Release of calcein from vesicle-beads (i.e. a decrease in the intensity) was observed due to the insertion of α-hemolysin into the vesicle membranes.

To directly observe the beads before and after calcein release, individual vesicle-beads before and after incubation with α-HL were imaged using a fluorescence microscope and images are shown in FIG. 4. Calcein-ABA-RBOE-PS-SA vesicle-beads before adding α-HL (FIGS. 4A-4C) show strong green fluorescence. After incubation with α-HL and rinsing with MOPS buffer (FIGS. 4D-4F), the green fluorescence from the beads decreased, demonstrating the reconstitution of α-HL, which formed pores in the membranes of the polymeric vesicles.

Characterization of MHC-I Proteopolymersome-Beads by Antibody Binding Tests

Integration of membrane protein in vesicle-beads was also demonstrated using in vitro synthesis. ABA-RBOE-PS-SA vesicle-beads were subjected to in vitro synthesis with or without MHC-I cDNA, i.e. the test sample and the control sample, respectively. Vesicle-beads retrieved from both the test and the control samples were tested for their binding with the two types of antibodies, the anti-His tag and the conformational anti-H-2Kb-OVA. Binding with anti-His tag and anti-H-2Kb-OVA demonstrates the presence of MHC-I in the vesicle-beads and the conformational folding of the integrated MHC-I protein, respectively.

Figure 5:
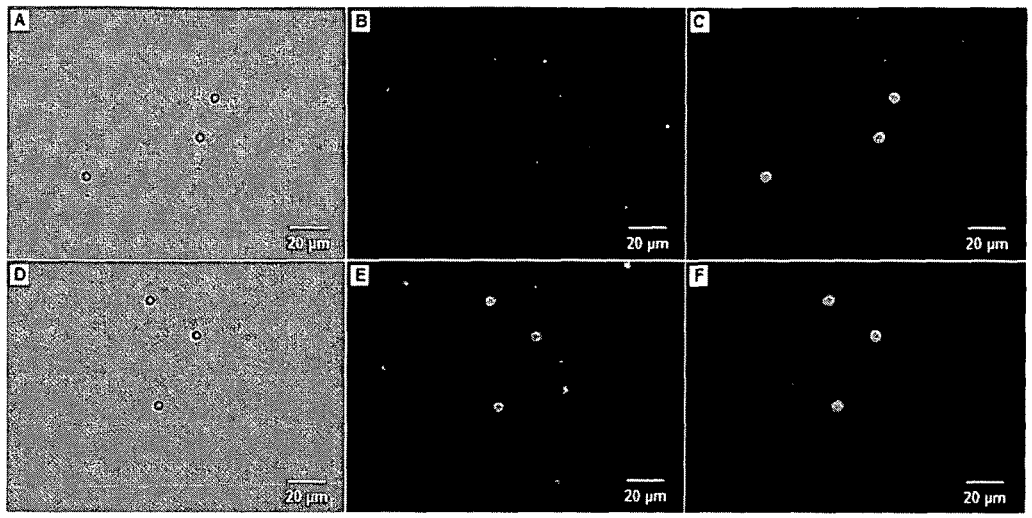
FIG. 5 shows optical micrographs of anti-His staining of vesicle-beads after in vitro synthesis (A)-(C) without or (D)-(F) with MHC-I cDNA. (A) and (D) relate to bright field images; (B) and (E) relate to fluorescence images after staining with secondary antibody labeled with Alexa Fluor® 488; (C) and (F) relate to fluorescence images showing vesicle-beads with vesicles labeled with a dye. The specific binding signal observed from vesicle-beads retrieved from in vitro synthesis with MHC-I cDNA (E) demonstrates the presence of MHC-I on vesicle-beads, i.e. the successful preparation of MHC-I proteopolymersome-beads.

FIG. 5 shows the results from the anti-His binding test. FIGS. 5A-5C and FIGS. 5D-5F are optical micrographs of the negative control beads ABA-RBOE-PS-SA and the vesicle-beads subjected to in vitro synthesis with MHC-I cDNA, respectively, after binding with anti-His and subsequently staining with secondary antibody labeled with Alexa Fluor 488. FIGS. 5C and 5F show that the ABA-RBOE polymeric vesicles remained on the beads after the binding test. By comparing FIG. 5B with FIG. 5E, it can be seen that the MHC-I membrane proteins were only present on the vesicle-beads subjected to in vitro synthesis with MHC-I cDNA, i.e. MHC-I proteopolymersome-beads were successfully obtained via the in vitro synthesis method.

Figure 6:
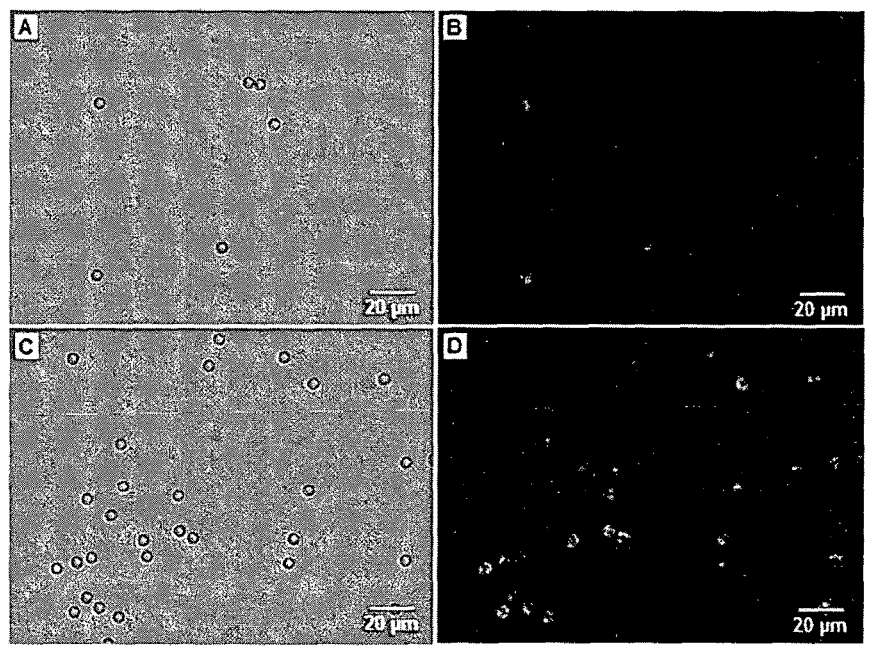
FIG. 6 shows optical micrographs of the conformational anti-H-2Kb-OVA staining of vesicle-beads after in vitro synthesis (A), (B) without or (C), (D) with MHC-I cDNA. (A) and (C) relate to bright field images; (B) and (D) relate to fluorescence images of vesicle-beads after staining with secondary antibody labeled with Alexa Fluor® 488. The specific binding signal observed from MHC-I proteopolymersome-beads shown in (D) indicates the proper folding of the membrane proteins in-vitro synthesized in the membranes of the vesicles carried on the 3D solid support.

The folding of the MHC-I membrane protein in MHC-I proteopolymersome-beads was tested via binding with the conformational antibody, anti-H-2Kb-OVA. MHC-I proteopolymersome-beads were incubated with anti-H-2Kb-OVA and then stained with secondary antibody labeled with Alexa Fluor® 488. The negative control vesicle-beads were subjected to the same binding protocol. Results are presented in FIG. 6. FIGS. 6A and 6B, and FIGS. 6C and 6D are optical micrographs of the negative control vesicle-beads and the MHC-I proteopolymersome-beads, respectively. Strong green fluorescence was detected from the MHC-I proteopolymersome-beads (FIG. 6D) but not the control vesicle-beads (FIG. 6B). The specific signal from the conformational anti-H-2Kb-OVA binding test demonstrates the proper folding of the integrated MHC-I membrane protein in the MHC-I proteopolymersome-beads.

Example 2

Drug binding assays were carried out to identify potential lead molecules targeting proteins. Scintillation Proximity Assay (SPA) is one of the homogeneous assays widely used to identify potentially new drug molecules targeting membrane proteins. It has been demonstrated below that the present proteopolymersomes on free floating 3D solid supports can be used in SPA for drug binding studies.

Methods

Proteopolymersomes with C-X-C chemokine receptor type 4 (CXCR4) were prepared as described in Example 1. The proteopolymersomes were incubated with different bead chemistry to attach the proteopolymersomes onto these beads as described in Example 1. For drug binding assays or SPA, the following commercially available beads with different surface chemistry and different core chemistry were used: WGA PVT SPA beads and PLL Ysi SPA beads for drug binding studies and SDF-1α$I^{125}$ as a hot ligand targeting CXCR4.

Figure 7:
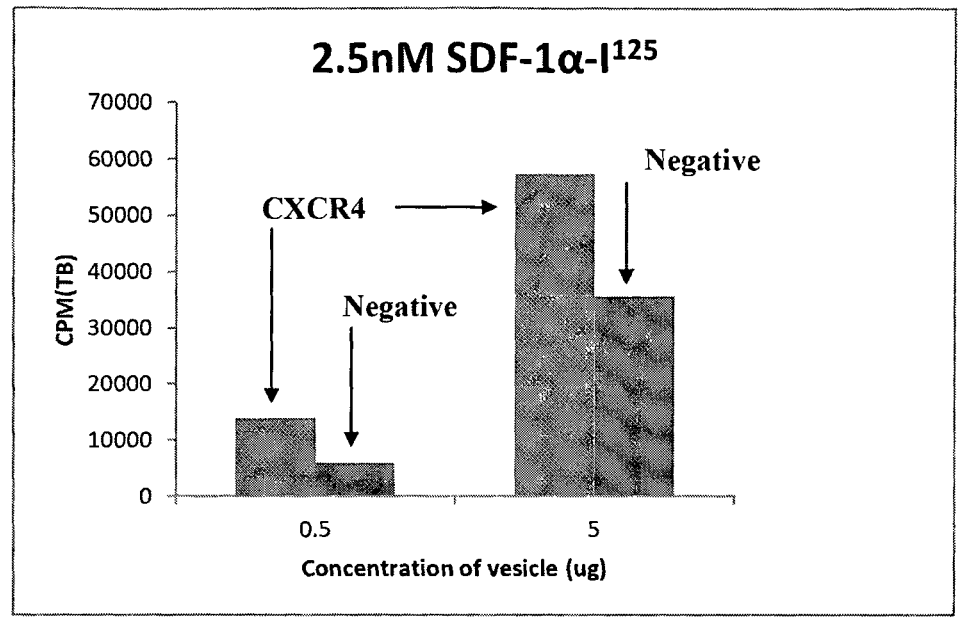
FIG. 7 shows the scintillation counts of [125I] SDF1-α (2.5 nM) ligand bound to the PVT-WGA beads coated with proteopolymersomes. Two different beads to polymersomes mass mixtures were taken for these experiments and were added in different wells. (Left set of bars represent 0.5 μg of polymersomes (with CXCR4 and without CXCR4 as negative) and 0.5 mg of PVT-WGA beads. Right set of bars represent 5 µg of polymersomes (with CXCR4 and without CXCR4 as negative) and 1 mg of PVT-WGA beads). After the constant amount of ligand is added to each well, they were incubated for 1 hour and read using Topcount NXT Scintillation counter.

Results 0.5 μg and 5 μs of proteopolymersomes with CXCR4 were incubated with 0.5 mg and 1 mg of WGA PVT SPA beads for two hours and 2.5 nM of SDF-1α$I^{125}$ was added and incubated for an hour and the specific binding of the ligand to CXCR4 proteopolymersomes were measured. Blank polymersomes were used as controls. From the FIG. 7, only proteopolymersomes with CXCR4 showed specific binding for the ligand.

Figure 8:
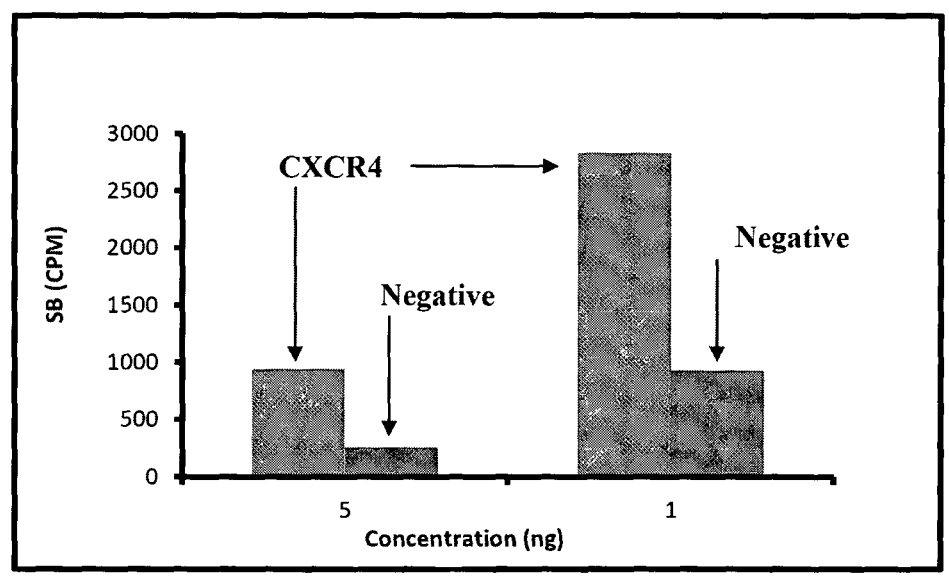
FIG. 8 shows the scintillation counts of [125I] SDF1-α (2.5 nM) ligand bound to the YSi-polylysine beads coated with proteopolymersomes. (Left set of bars represent 5 ng of polymersomes (with CXCR4 and without CXCR4 as negative) and right set of bars represent 1 ng of polymersomes (with CXCR4 and without CXCR4 as negative) coated to 0.2 µg of YSi-polylysine beads). After the constant amount of ligand is added to each well, they were incubated for 1 hour and read using Topcount NXT Scintillation counter.

1 and 5 ng of proteopolymersomes with CXCR4 was incubated with 0.2 ug of PLL Ysi SPA beads for two hours and 2.5 nM of SDF-1α$I^{125}$ was added and incubated for an hour and the specific binding of the ligand to CXCR4 proteopolymersomes were measured. Blank polymersomes were used as controls. From FIG. 8, it is clear that only the proteopolymersomes with CXCR4 shows specific binding for the ligand.

Figure 9:
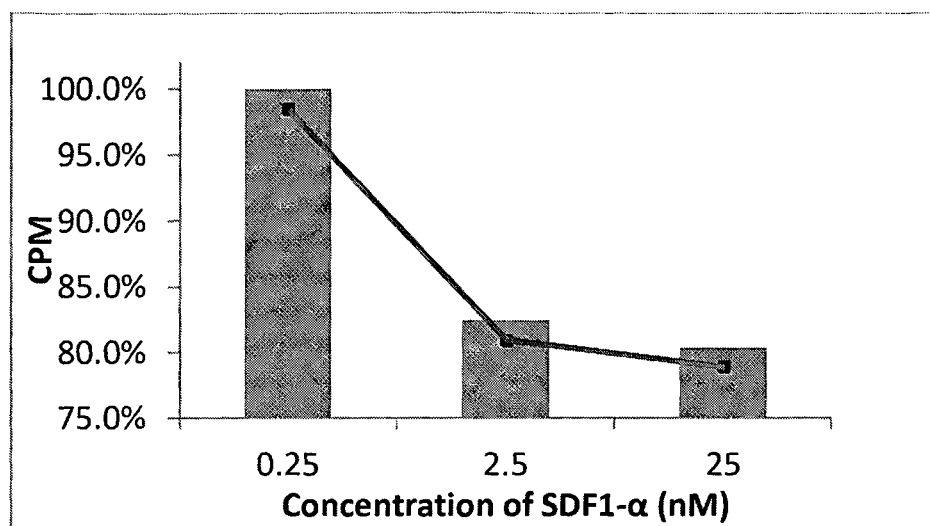
FIG. 9 shows the scintillation counts of [125I] SDF1-α (2.5 nM) bound to the PVT-WGA beads (0.1 µg) coated with proteopolymersomes with CXCR4 (5 µg) in the presence of varying concentrations of non-labeled SDF1-α (0.25, 2.5 and 25 nM). The mixtures were incubated for 90 minutes and read using Topcount NXT Scintillation counter.

Based on these results, an optimized vesicles-bead ratio was selected to carry out competition binding assay. In the competition binding assay, 5 μg of proteopolymersomes with 0.1 μg of beads were incubated with 2.5 nM of SDF-1α$I^{125}$ and varying concentration of SDF-la (0.25, 2.5 and 25 nM) were added to obtain a dose response behavior for proteopolymersomes with CXCR4. From FIG. 9, a dose response behavior for proteopolymersomes on beads for three different concentrations of SDF-la could be obtained.

By "comprising" it is meant including, but not limited to; whatever follows the word "comprising". Thus, use of the term "comprising" indicates that the listed elements are required or mandatory, but that other elements are optional and may or may not be present.

By "consisting of" is meant including, and limited to, whatever follows the phrase "consisting of". Thus, the phrase "consisting of" indicates that the listed elements are required or mandatory, and that no other elements may be present.

The inventions illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

By "about" in relation to a given numerical value, such as for temperature and period of time, it is meant to include numerical values within 10% of the specified value.

The invention has been described broadly and generically herein. Each of the narrower species and sub-generic groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

The invention claimed is:

1. An artificial cell membrane system comprising:
   (i) at least one supported membrane protein carrier comprising a polymeric vesicle comprising a circumferential membrane comprising amphiphilic block copolymers, wherein at least one protein is integrated, embedded or inserted in the circumferential membrane of amphiphilic block copolymers via in vitro synthesis, wherein the supported membrane protein carrier comprises a mean diameter of less than 500 nm; and
   (ii) a free floating polystyrene microsphere (PS-SA) bead or scintillation proximity assay (SPA) bead suspended in a fluid medium, wherein the PS-SA bead or SPA bead comprises a mean diameter of less than 5 µm,
   wherein the at least one supported membrane protein carrier comprises a direct attachment to a surface of the PS-SA bead or SPA bead, wherein the direct attachment comprises a physisorption attachment, a chemisorption attachment, or combinations thereof, and wherein the surface of the PS-SA bead or SPA bead is decorated with the polymeric vesicle.

2. The artificial cell membrane system of claim 1, wherein the polymeric vesicle has a circumferential membrane comprised of the same or different amphiphilic block copolymer.

3. The artificial cell membrane system of claim 2, wherein the amphiphilic block copolymer is synthetic.

4. The artificial cell membrane system of claim 1, wherein the at least one membrane protein carrier comprises a functional group facilitating the direct attachment to other supported membrane protein carrier.

5. The artificial cell membrane system of claim 4, wherein the functional group is an imino, amino, mercapto, carboxylic acid group, biotin, streptavidin, or click chemistry group.

6. The artificial cell membrane system of claim 1, wherein the direct attachment comprising a physisorption attachment, a chemisorption attachment, or combinations thereof is selected from the group consisting of Van der Waals interaction, hydrogen bonding, hydrophobic interaction, solvation force, electrostatic interaction, and Casimir interaction.

7. The artificial cell membrane system of claim 1, wherein the direct attachment comprising a physisorption attachment, a chemisorption attachment, or combinations thereof is by covalent bonding.

8. The artificial cell membrane system of claim 1, wherein the system comprises additional supported membrane protein carriers.

9. The artificial cell membrane system of claim 1, wherein each free floating PS-SA bead or SPA bead carries at least 10 supported membrane protein carriers.

* * * * *